United States Patent [19]

Ferrara et al.

[11] 4,112,924
[45] Sep. 12, 1978

[54] BLOOD COLLECTION VALVE

[76] Inventors: Louis Thomas Ferrara, 2988- Ave. T;
Janet Roccisano, 2169- E. 36th St.,
both of Brooklyn, N.Y. 11229

[21] Appl. No.: 785,656

[22] Filed: Apr. 7, 1977

[51] Int. Cl.² .............................................. A61B 5/00
[52] U.S. Cl. ............................ 128/2 F; 128/218 NV;
128/DIG. 5
[58] Field of Search ......... 128/2 F, DIG. 5, 218 NV,
128/276, 274; 137/854

[56] References Cited
U.S. PATENT DOCUMENTS

| 3,066,856 | 12/1962 | Frank | 137/854 X |
| 3,228,409 | 1/1966 | Godel | 137/854 X |
| 3,610,273 | 10/1971 | Russell | 137/854 X |

FOREIGN PATENT DOCUMENTS 2,349,996  2/1974  Fed. Rep. of Germany .... 128/DIG. 5

Primary Examiner—John D. Yasko

[57] ABSTRACT

A means to prevent backflow during vena-puncture by employing a one way valve in conjunction with an evacuated tubular element which has at its opened end a resilient stopper which is used to house or contain said valve and which acts as a sealant for the system. The stopper allows penetration by a special two-ended cannula which is threaded into a holder used to hold the tubular element during vena puncture. Blood flows from the vein, through the cannula, into the hollow portion of the stopper containing the valve and subsequently into the tubular element for storage. During blood collection, blood is prevented from backflowing by the closing action of the valve. In this manner contamination to the patient by particulate matter within the tubular element is prevented.

4 Claims, 7 Drawing Figures

BLOOD COLLECTION VALVE

The invention in essence relates to a mechanism or valve which prevents or minimizes backflow of blood from within a collection tube back into the patients blood system while phlebotomy is in progress.

BACKGROUND TO INVENTION

Blood for diagnostic purposes is presently drawn in a system comprising a glass evacuated tube fitted by a rubber stopper to seal said tube from the outside enviornment. A plastic cylindrical holder is used in conjunction with a special needle with two sharpened ends. One end of said needle is designed to be threaded into one end of holder. A tube can then be inserted within said holder to meet one end of sharp needle. When vena puncture is made the tube within the holder is pressed firmly foward wherein the end on the needle within holder penetrates rubber stopper and allows blood to flow into tube due to negative pressure or evacuation of tube. When the pressure within the tube equals the pressure of blood entering, no blood flows. It can however be demonstrated experimentaly and confirmed by computations that it is possible under certain conditions for backflow to occur during this process especially at the point of removal of tourniquet while needle is still within patient's vein.

It is with this problem in mind that the invention described herein offers for the first time a novel method of eliminating or minimizing the hazards of backflow.

SUMMARY OF INVENTION

In essence the invention incorporates a mechanical device which acting as a one way valve allows blood to enter into an evacuated blood collection tube and prevent said blood from flowing in the opposite direction i.e., return to patient's vein via needle. Such a device is presently not on the market and to our knowledge is novel.

Broadly the invention may be defined as a one way valve fitted within a rubber stopper which is part of a blood collection tube acting as a seal and a means of penetration.

The invention is a circular plastic disk approximately 0.5 centimeters in diameter and 2mm thick. The disk has triangular openings. Affixed to the face or flat surface of said disk at its center by a plastic rivet is a thin walled rubber membrane substantially thinner than the disk but approximately the same diameter. Behind the thin membrane is another circular disk, being a duplicate of the disk previously described and held by the same rivet which holds the membrane at its center to the other disk. In other words the membrane is secured at its center by a rivet and held between the two duplicate disks. The design is such that the thin membrane sandwiched between the two plastic disks is riveted so that all three components are held together as one entity. In this manner the membrane is allowed to vibrate or occilate within certain limits goverened by the spacing between the two disks, at its periphery. Said membrane being kept true or not allowed to distort as it is checked by both plastic disks. Thus a needle penetrating the rubber stopper will allow one to push material into the tube but suctioning material out of the tube will cause the membrane to close tightly against the outer edges of the disk and thus seal off the tube from the inner portion of the stopper.

DETAILS OF DRAWING

Figure 1:
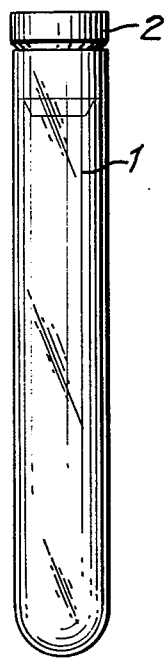
FIG. 1 shows a blood evacuated blood collection tube (1) with stopper (2) inserted.
Figure 2:
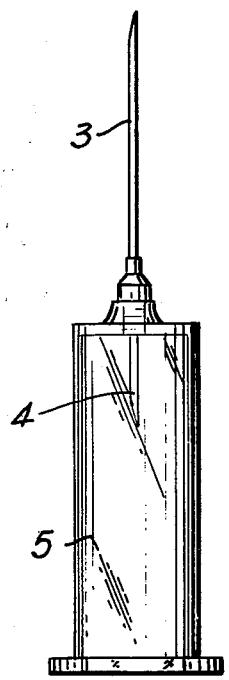
FIG. 2 shows a plastic holder (5) with attached needle, double ended (3) and (4).
Figure 3:
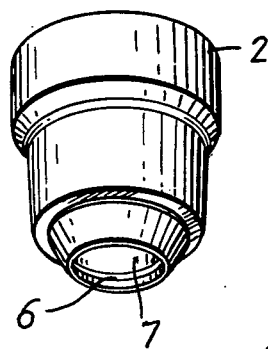
FIG. 3 shows enlarged rubber stopper which is used to seal system

An evacuated tube FIG. 1 (1) is fitted with a stopper (2) typically constructed of rubber and is used to preserve the integrity and evacuation properties of the system. When phlebotomy is to be accomplished, said tube (1) is inserted into the special holder (5) FIG. 2 which was previously fitted with a double ended needle (3) & (4). When vena puncture is made with front end of needle (3) Tube (1) is pressed in a foward direction up against the back end of needle (4) subsequently penetrating stopper (2) thereby allowing said portion of needle to have access within the confines of the hollow portion of stopper (2), FIG. 3. (7) . Since the container or tube (1) has previously been evacuated, blood is forced in the direction from within said stopper (2), (7) and towards the bottom of the glass tube (1).

As previously mentioned, it is possible while phlebotomy is in progress for some blood to flow in the opposite direction ie. back into the patient's vein. In order to avoid this, the invention (valve) FIG. 4, has been previously snapped into place in groove (6) FIG. 3, within the hollowed portion (7) of stopper (2). This valve is shown as it would appear installed in FIG. 5, Hence if pressure on the patient's side of the system (venous pressure) becomes greater, ie. tends to suck or withdraw blood from said tube (1) the valve (diaphram) will close and seal the system so that in effect no blood can flow from within the confines of tube (1) back into the patient's blood system.

Figure 4:
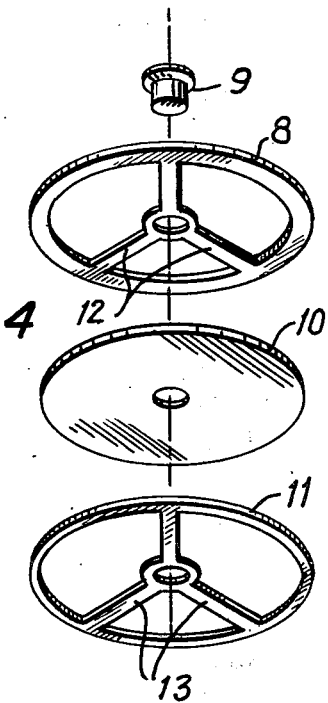
FIG. 4 shows enlargement of invention (valve) as it appears with its components seperated.
Figure 5:
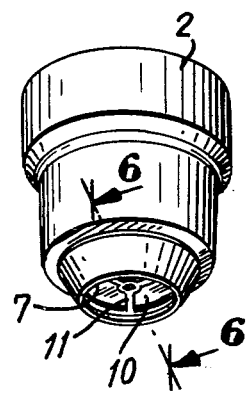
FIG. 5 shows enlargement of rubber stopper (2) with insertion of invention (valve) FIG. 4.

The valve FIG. 4, is so designed that it can be snapped into place in groove (6) within the hollow confines (7) of stopper (2) so that it provides a sealant as well as escapement system for the blood fluid. In essence we speak of a one way valve system which allows blood to flow into said tube (1) but not out in the opposite direction ie. patient's venous system etc.

Figure 6:
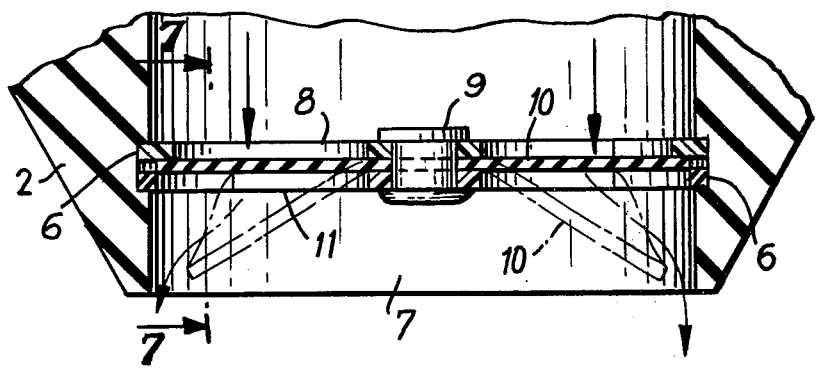
FIG. 6 shows enlarged cross section of stopper (2) with invention (valve) exposed within the confines of said stopper.
Figure 7:
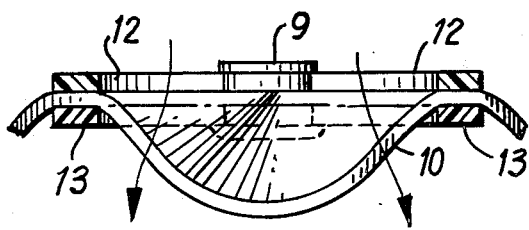
FIG. 7 shows enlarged side view of valve with opened diaphram (10) as it would appear as blood flows into the tube (1)

This valve basically consists of three elements, two of which are supportive and substantially rigid (11) and (8) compared to the third element (10) FIG. 4, which is a diaphram which is substantially flexible. The supportive members or elements (8) and (11) are basically two similar elements of plastic or other suitable material, being circular in shape and having spoke-like members (13) and (12) with orifices at their respective centers so that in essence there appears a wheel like arrangement of members oriented in a hub and spoke system. The diaphram (10) is of substantially thin rubber-like material elastic in essence, and having an orifice located at its center thus allowing itself to be sandwiched inbetween elements (8) and (11) and thereby all three components being secured by a rivet-like element (9) at their respective centers form an integrated valve system. In essence therebeing a flexible membrane (10) sandwiched inbetween two rigid elements (11) and (8). The membrane (10) is always touching element (8) or mates with said element especially well at its circumferential portion. Being fitted securely at its center to (8) and (11) its motion or opening capacity is smallest at its center where the rivet secures it and movement or opening capacity increases from the center towards the periphery of the diaphram. Thus the widest opening FIG. 6. will occur at the periphery of the diaphram as blood is forced inwardly into the tube (1). Upon completion of blood withdrawal or if pressure in the opposite end should occur the diphram will snap shut, its circumferential or peripheral portion being closed securely or mating against the peripheral wall of rigid element (8). Normally the diaphram is in the closed position and in this manner the rubber stopper (2) which houses the valve thereby being a integral part of said stopper can if desired be autoclaved or sterilized rather than the entire system. The element (11) acts as a supportive structure and to keep the diaphram from opening too wide and thereby distorting the diaphram to the extent that its intended function is lost. This element (11) is so spaced behind element (10) (diaphram) that it thus governs the movement of the diaphram. In essence it is substantially that it does not hinder the movement of the diaphram (10) in the direction of blood flow. It is to be noted that the entire valve or integrated valve components are placed within a location within the hollow portion (7) of the stopper (2) so that there exists a spacing between the penetrating needle (4) and the valve in such a manner that there is no obstruction to said valve by said needle. Pending mechanical inovation and suitable material it would be possible to eliminate element (11). It is included in the invention to emphasize the fact that diaphram (10) must be of such material or related in such a constructive framework of related elements that it must stay closed against supportive structure (8) until blood flows into the system by forcing said diaphram opened. Converely it should then close properly at completion of blood withdrawal or should the aforementioned backflow occur in the interim of collection.

It is within the scope and spirit of the above described invention to make such variations and modifications and substitutions of equivalents as would be obvious to a person skilled in this particular art.

We claim:

1. A non-return, or one way blood collection valve assembly essentially comprising in combination: three thin walled circular disk-like elements, two of which are substantially rigid, and having nearly the same diameter act thereby as supportive structures for the third element, which being of a diameter substantially intermediate of the other two elements and also thinner, is sandwiched inbetween said rigid elements, being affixed thereto by suitable means such as a rivet at the center of the entire assembly and being able to oscillate such as in an open and closed position intermittently said thinner element or membrane acts by flexion to allow blood to pass or enter in one direction whereby said valve assembly is held in place by the larger of the ridged elements at its circumferential edge within the confines of a hollow stopper-like element by a ridge that circumscribes the inner wall of said stopper; and said stopper being of a compliant nature such as rubber so as to allow intermittent penetration of a cannula, is used to intermittently seal the opened end of an elongated tubular element which has been previously evacuated substantially of air and serves thereby to recieve and store blood as it enters via said cannula and pass the valve.

2. A circular thin-walled flat membrane as described in claim 1 which is of such material or consistency that allows it to oscillate or flex intermittently in a closed or opened position thereby allowing blood to flow in one direction only from cannula pass the valve and into a receiving vessel or tubular element.

3. Two thin wall circular substantially rigid components as described in claim 1 each in a wheel-like arrangement having spoke-like projective elements acting together to support a flexible membrane sandwiched inbetween; and the larger of the two rigid components being used to secure the entire assembly within a hollow portion of rubber stopper.

4. The smaller of the rigid circular elements as described in claim 3 being secured to the flexible membrane and larger rigid circular element at their centers is substantially spaced from the face of the membrane so that it provides a means to prevent distortion of said membrane in the opened position, while at the same time its smaller diameter allows clearance for the membrane to flex and thus allow blood to pass.

* * * * *